United States Patent
Desvaud

(10) Patent No.: US 7,503,680 B2
(45) Date of Patent: Mar. 17, 2009

(54) STRIPLIGHT AND SYSTEM WITH HIGH-POWER LIGHT-EMITTING DIODES FOR AN AUTOMATIC FAULT DETECTION SYSTEM

(75) Inventor: Jean-Louis Desvaud, Les Essarts le Roi (FR)

(73) Assignee: Siemens Vai Metals Technologies SAS, Saint-Chamond (FR)

( * ) Notice: Subject to any disclaimer, the term of this patent is extended or adjusted under 35 U.S.C. 154(b) by 142 days.

(21) Appl. No.: 11/637,402

(22) Filed: Dec. 12, 2006

(65) Prior Publication Data

US 2007/0171661 A1 Jul. 26, 2007

(30) Foreign Application Priority Data

Dec. 16, 2005 (FR) .................................. 05 13105

(51) Int. Cl.
*F21V 7/04* (2006.01)
(52) U.S. Cl. ..................... 362/555; 362/551; 362/558
(58) Field of Classification Search ................ 362/555, 362/800, 551, 558, 227, 230, 231, 240–248
See application file for complete search history.

(56) References Cited

U.S. PATENT DOCUMENTS

| | | | | |
|---|---|---|---|---|
| 4,847,734 A | * | 7/1989 | Katoh et al. ................ | 362/555 |
| 5,032,960 A | * | 7/1991 | Katoh ......................... | 362/240 |
| 5,810,463 A | * | 9/1998 | Kawahara et al. ........... | 362/601 |
| 6,357,904 B1 | * | 3/2002 | Kawashima ................ | 362/555 |
| RE37,740 E | | 6/2002 | Chadwick et al. | |

| | | | |
|---|---|---|---|
| 2002/0006039 A1 | 1/2002 | Ueda et al. | |
| 2003/0156416 A1 | 8/2003 | Stopa et al. | |
| 2005/0201097 A1 | 9/2005 | Kiraly et al. | |

FOREIGN PATENT DOCUMENTS

| | | |
|---|---|---|
| JP | 60 146134 | 8/1985 |
| JP | 10 282015 | 1/1999 |

OTHER PUBLICATIONS

Domjan L. et al.: "Stripe illuminator based on LED array and parabolic mirror for active triangulation sensors used on mobile robots" Optical Engineering SPIE USA, vol. 39, No. 11, (Nov. 2000), pp. 2867-2875, XP002389564 ISSN: 0091-3286.

* cited by examiner

*Primary Examiner*—Bao Q Truong
(74) *Attorney, Agent, or Firm*—Bachman & LaPointe, P.C.

(57) ABSTRACT

Process for lighting in cold light of a scrolling product for the acquisition of images by linear digital cameras for a fault detection system, by a device comprising a light source constituted by high-power light-emitting diodes. According to this process, the light-emitting diodes are arranged in at least one row, aligned according to equal intervals, in a housing constituting a type of light box with reflecting walls, slight diffusion is produced from the light coming from the light-emitting diodes by a film closing the light box and the light beams exiting from the light box are concentrated by a reflecting device into a flat and narrow lighting spot beam, whereof the width is substantially equal to the length occupied by the alignment of the diodes. The lighting device is closed by an envelope constituted by an air-tight tube blocked at its two ends and provided with a window fitted with a transparent pane arranged substantially over the entire length of the envelope to let the illuminating light pass through. The air-tight tube is ventilated and cooled.

19 Claims, 2 Drawing Sheets

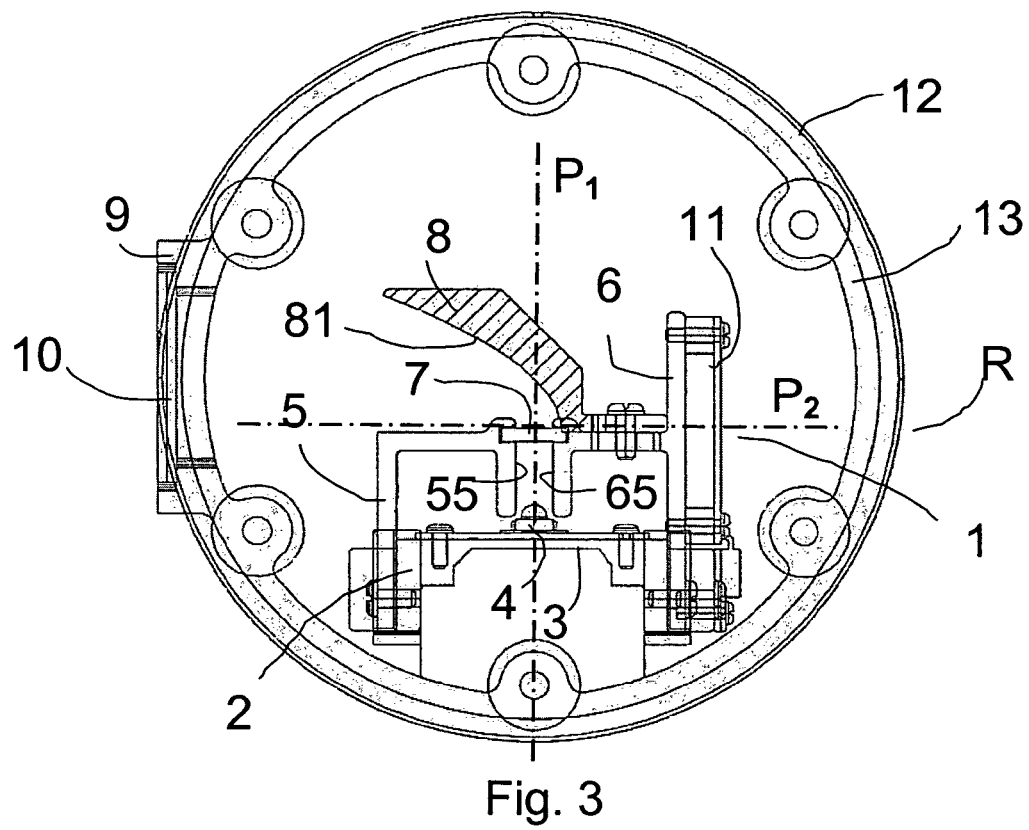
Fig. 3
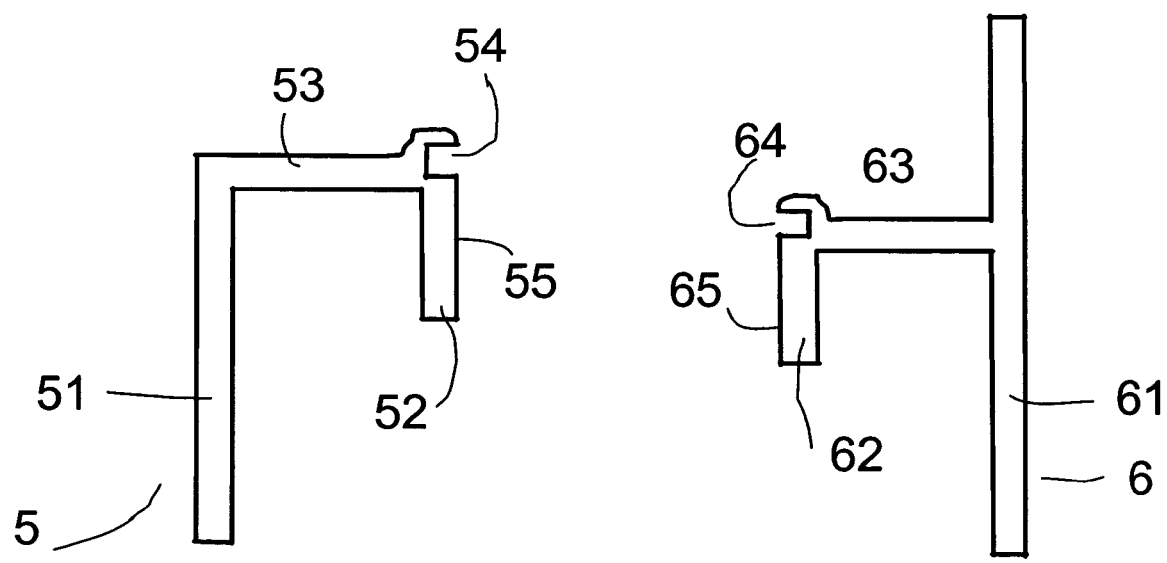
Fig. 4a
Fig. 4b

STRIPLIGHT AND SYSTEM WITH HIGH-POWER LIGHT-EMITTING DIODES FOR AN AUTOMATIC FAULT DETECTION SYSTEM

FIELD OF THE INVENTION

The present invention relates to a lighting device using high-power light-emitting diodes. It applies to lighting devices in the form of striplight to be integrated in fault-detection systems. It is particularly adapted to ensure the lighting function in automatic inspection systems of products in the form of a strip and especially in surface inspection of laminated metallic strips.

PRIOR ART

For some years, automatic inspection systems of strip products have been developed. The advantage of these techniques is being neither restrictive for the operator, nor subjective and they can be used on production lines without requiring the use of a specific line for inspection representing immobilization of material, human means and stored product diverted from the normal sending circuit. It is however indispensable that these automatic devices be highly reliable in terms of detecting faults, and they should neither let them through, which might penalize quality, nor detect them in surplus what might penalize productivity.

In general these devices are composed of imaging means whereof the optical axis is directed to the surface to be inspected. These devices generally comprise a camera fitted with a lens for concentrating the light beams originating from the product to be observed onto a photosensitive sensor constituting the detection device. It is necessary to form an image of the surface of the product to be inspected on the detection device. First of all, the different types of cameras available capable of acquiring images corresponding to a certain visual field, following the example of methods utilized for television, were used; the defined field thus corresponds to the zone to be inspected. This method needs powerful lighting obtained by conventional means, such as fluorescent neon lamps. These devices have produced initial results, though the images obtained lack the contrast necessary for automatic classification of the images and for identification of faults. It is in fact necessary to form images with a fairly fine resolution so as to be able to detect faults whereof the size of certain details is reduced.

Digital cameras of the matrix type and different lighting devices have been used, such as striplight with light-emitting diodes functioning by pulses and producing flashes of light. Fiber optics for guiding the light closest to the zone to be observed have also been used. But the use of matrix cameras has disadvantages, as they exhibit in particular faults on the image in the zones of the edges and angles. During development of sensors photosensitive to load transfer, known as CCD sensors, the applicant company has proven that these digital sensors were able to improve the sensibility and reliability of fault detection devices, in particular by eliminating angle faults by integrating them, mounted on rods, into linear cameras. In fact, these cameras produce the image of a line on the surface of the strip at a single take and a two-dimensional image of the surface of the strip can be reconstituted by making successive acquisitions of images of the scrolling product. An image of the surface of the product is thus made from the acquisition of a succession of lines. But it is then necessary to arrange lighting means whereof the light characteristics are constant and defined, or at least controlled. It is in fact indispensable to have controlled lighting conditions for the acquisition of an image line by line.

Further, in certain applications it is interesting to combine observation of the product under the lighting provided by the additional light and that coming from the light emitted by the product itself when it is hot enough to emit in the infrared light field. It is therefore particularly interesting to design a lighting device capable of providing cold light, that is, a light which does not contribute any heat energy to the product to be observed, and to provide such constantly and continuously.

Finally, utilizing automatic surface inspection devices imposes constraints, in particular due to their bulk, and they are not always easy to respect, and it is also necessary to provide devices, which are compact, tight and cooled so that they can function in a severe industrial ambiance. The effect of this is the necessity to install the fault detection equipment at variable distances from the product to be observed, as per application, such as for example at the outlet of a cold thickness calender or at the outlet of a hot thickness calender. It is therefore reasonably interesting to design a single lighting device whereof the illumination is produced by a spot beam of parallel beams whereof the convergence on the product to be observed does not vary with distance.

Finally, it is advantageous to have a system capable of working on several colors so as to be able to filter the perturbations caused by ambient lighting or by the surrounding atmosphere.

SUMMARY OF THE INVENTION

The aim of the device of the invention is to resolve all these problems by creating a lighting device whereof the characteristics are controlled to be utilised in an inspection system utilizing a high-performance linear digital camera. The whole of the fault detection device can have a reduced footprint, enabling its installation in the immediate vicinity of the scrolling strip. This helps protect the whole device from the environment, helps cool it and ventilate it if ambient conditions require it. The device can easily be installed in a limited free space and means for extraction of expelled moisture or any other agent, which might pollute the space in which the light forming the images to be detected and analyzed, must be spread can also be installed.

According to the invention the lighting device (R) of a scrolling product (S) for detection of surface faults is constituted by a closed mechanical support assembly (1) forming an elongated box, constituting a striplight and comprising:

a plurality of high-power light-emitting diodes (4) aligned in at least one row and arranged side by side according to a regular pitch, a reflecting light guide with flat walls (55, 65), parallel to one another and located in planes substantially parallel to that ($P_1$) formed by the axes of the light-emitting diodes, a film made of translucent and diffusing material (7) arranged on the trajectory of the light beams emitted by the light-emitting diodes, a reflector (8) for concentrating and sending back the light beams to the exterior of the closed support (1) through a window (9) forming an elongated opening arranged substantially over the length of the striplight, a transparent lid (10) for closing the opening arranged in the striplight while letting the light beams originating from the light-emitting diodes (4) pass to the exterior.

According to the invention the walls (55, 65) of the light guide are advantageously made of polished metal, and also the film diffuser (7) is made of roughened Plexiglas.

According to a preferred embodiment of the invention the surface (81) of the reflector (8) is a straight parabolic cylinder. The reflector (8) is arranged such that its axial plane ($P_2$) is substantially perpendicular to the plane ($P_1$) defined by the axis of the light-emitting diodes (4). This arrangement is such that the intersection of the plane ($P_1$) defined by the axis of the diodes with the axial plane ($P_2$) of the reflector (8) is substantially located on the axis joining the focal spots of the parabolic sections of the reflector.

The mechanical support (1) of the lighting device (R) of a scrolling product (S) is still preferably closed by an envelope constituted by an air-tight tube (13) blocked at its two ends and provided with a window (9) fitted with a transparent pane (10) arranged substantially over the entire length of said envelope to let the illuminating light pass through. The airtight tube (13) is ventilated and cooled.

According to an advantageous embodiment of the invention, the light-emitting diodes (4) are connected electrically in series in groups and form a chain. An adjustable current controller feeds each chain.

Temperature sensors are installed in the airtight tube (13) to measure the average internal temperature.

The striplight (R) assembly carries fixing means adjustable for orienting and adjusting the lighting of the zone to be observed.

The process of the invention allows lighting in cold light of a scrolling product (S) for the acquisition of images of the surface of said product by linear digital cameras (C) for a fault detection system, by means of a device comprising a light source constituted by high-power light-emitting diodes (4), according to which process the light-emitting diodes (4) are arranged in at least one row, aligned according to equal intervals, in a housing constituting a sort of light box with reflecting walls (55, 65), slight diffusion of the light coming from the light-emitting diodes is produced by a film (7) closing the light box and the light beams exiting from the light box are concentrated by means of a reflecting device (8) into a flat and narrow lighting spot beam, whereof the width is substantially equal to the length occupied by the alignment of the diodes.

According to the process of the invention, the distance of the film (7) closing the light box with light-emitting diodes (4) is determined as a function of the implantation pitch of said light-emitting diodes, the film (7) closing the light box being constituted by a roughened transparent material, such as roughened Plexiglas.

Still according to the process of the invention the reflector (8) sends the light beams back in a direction substantially perpendicular to the axis of emission of the light-emitting diodes (4), the surface (81) of the reflector (8) having the form of a straight parabolic cylinder.

According to the invention the light beams constitute a flat lighting spot beam and are substantially parallel to one another.

Still according to the invention, the light-emitting diodes (4) contained in the same striplight (R) are all of the same color, this color being white, red or green.

According to the process of the invention the light-emitting diodes (4) are connected electrically in series in groups constituting a chain, the light-emitting diodes (4) contained in the same striplight (R) having an equal unit power and of the value of 1, 3 or 5 watts.

BRIEF DESCRIPTION OF THE DRAWINGS

But the invention will be better understood from the description of an embodiment.

FIG. 3 illustrates in section a striplight according to the invention.

FIG. 4a illustrates the detail of a piece forming the light guide.

FIG. 4b illustrates the detail of another piece forming the light guide.

DETAILED DESCRIPTION OF THE PREFERRED EMBODIMENT(S)

Figure 1:
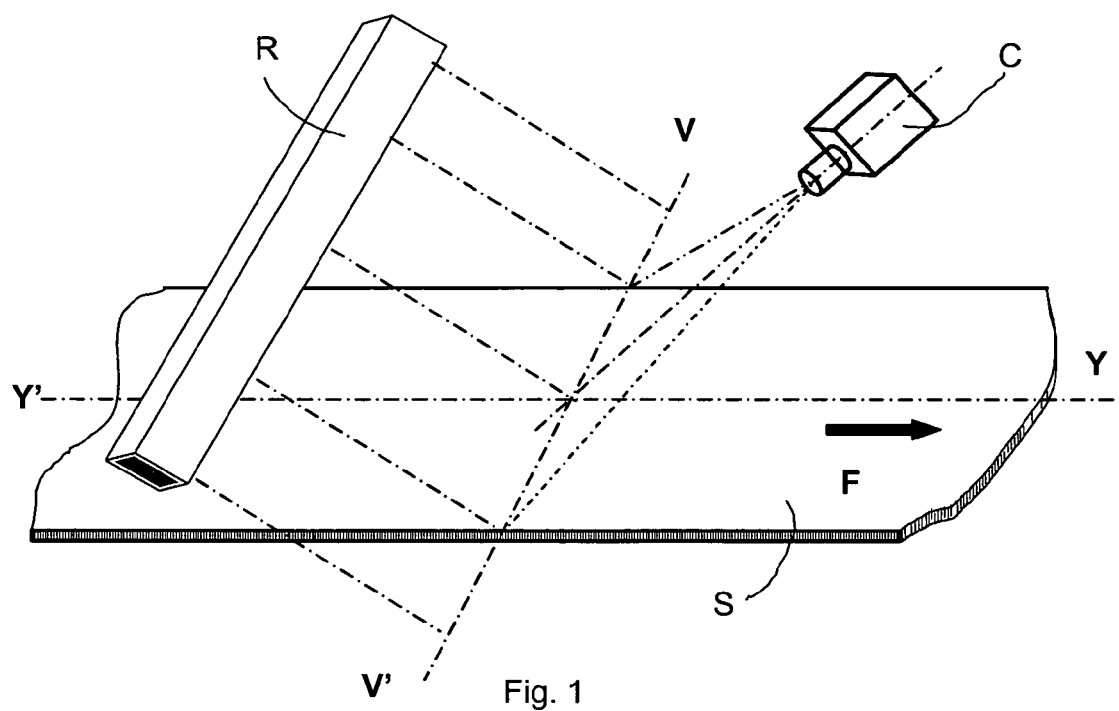
FIG. 1 illustrates a fault detection device according to the invention.

FIG. 1 schematically illustrates an arrangement of a fault detection system of the surface of a product S scrolling F, and optionally faults also present beneath the surface. A flat product in the form of a strip S is illustrated, that is, a product whereof one dimension, the width of the product, perpendicular to the direction of scrolling is far greater than the third, the thickness of the product. It is for this case of a figure that the process of the invention draws all its interest, but it can be applied also to other types of products. According to the process of the invention a linear camera C of type CCD is used, and is oriented so as to form on the rod of sensitive sensors the image of a line V'V passing through the strip S.

The whole of the light beams reflected by the strip S whereof the direction general is that of the optical axis and which are thus concentrated by the lens are contained in an angular sector or volume known as opening angle. Their intersection with the surface of the product forms an optical sighting line V'V generally transverse relative to the scrolling axis Y'Y of the strip S. A lighting system R illuminates a portion of the scrolling strip at the level of the optical sighting line. A device for real-time acquisition of images registers a succession of views taken by the linear camera according to the optical sighting line V'V. A two-dimensional image of the surface of the strip is then reconstituted by joining the succession of images taken by the linear camera C of the surface of the scrolling product S.

Finally, signal-processing systems enable real-time analysis of images delivered by the view-taking apparatus. The choice of a linear camera provides images without deformation and this allows limiting of the lighting device to illumination of a narrow strip encasing the optical sighting line V'V. This provides a lighting device whereof the parameters of the light are controlled and constant. It is in fact vital that variations in lights cannot be registered as potential faults of the surface of the strip. Furthermore, according to the process of the invention the strip is illuminated with a lighting spot beam whereof the beams are parallel, and in this way any problem of focusing of the light beam on the strip can be overcome, and the distance from the striplight R to the strip does not require any particular adjusting.

Figure 2:
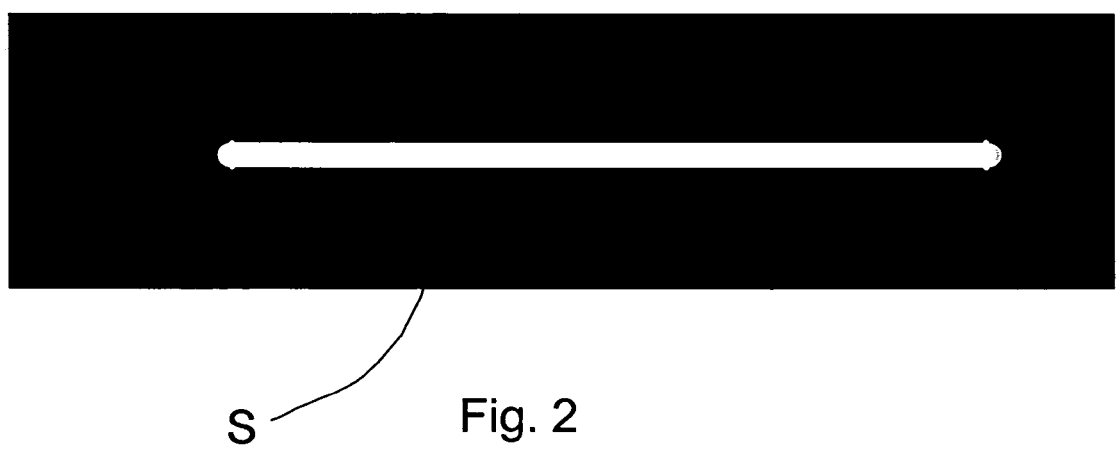
FIG. 2 illustrates an image of the lighting obtained by the process of the invention.

FIG. 2 illustrates the image of the lighting of a white surface obtained by the process of the invention. The width of the spot beam is defined for the maximal width of the strip S, the width of its impact according to the direction of scrolling F and the light intensity are constant over the entire width of the product S.

The lighting process of the invention utilizes as light source light-emitting diodes, which are sources of slight dimension, which can be installed at to a relatively reduced pitch to constitute a homogeneous and constant beam. The emission from these diodes is produced according to a volume of axial revolution whereof the distribution is close to a gaussien. The process of the invention utilizes the diffusion of light through a film to at best equalize the light flux according to the direction of the length of the striplight and the reflection onto a parabolic mirror to direct the light beams in a common direction so as to form a spot beam of beams parallel to one another.

FIG. 3 shows a section of the striplight according to an embodiment of the invention. The striplight can have a general tubular form closed at its two ends by circular terminals. A support chassis 1 is made by means of, for example, profiles and plates assembled by bolting so as to be disassembled also. These pieces constitute the length of the striplight and carry at their ends the closing circular terminals 12. A base 2 carries in its central part a plate 3, which receives the light-emitting diodes 4, aligned in a single row. This plate 3 is preferably made according to the printed circuits technique allowing conventional fixing of the light-emitting diodes by welding the feet of the components onto the printed circuit. This technique also directly makes the connections in series, or according to another mode, light-emitting diodes as a function of the supply mode, which has been retained.

Two pieces 5 and 6 are fixed on the base 2 to make up the light box and support the optical device of the invention. These pieces are illustrated in detail in FIGS. 4a and 4b. These pieces 5, 6 respectively are, for example, made by extrusion or molding, and they each comprise respectively two parallel wings 51, 52 and 61, 62 connected by a core, respectively 53 and 63. The length of these pieces is approximately that of the row of diodes and are fixed, for example, by bolting, onto two parallel side faces of the base 2. The fixing is done such that the external faces 55 and 65 of the pieces 5 and 6 are parallel to one another. The wings 51, 52, respectively 61, 62 are of different heights and calculated so that the shortest wings enclose the row of light-emitting diodes 4. In the same way, the dimension of the cores 53 and 63 is calculated relative to the width of the base 2 to create this arrangement, illustrated in FIG. 3.

Therefore, the assembly 1 forming a support chassis of the different components also constitutes a closed light box. The wings 52 and 62, respectively pieces 5 and 6, form a light guide whereof the walls enclose the row of light-emitting diodes. The inner faces of this conduit are the outer faces 55 and 65 respectively of pieces 5 and 6, and are parallel to one another and are made of polished metal to be reflecting. Thus, all the light beams emitted by the light-emitting diodes inside the volume of axial revolution of emission of each will be directed to the outlet of the light guide constituted by the faces 55 and 65 of the pieces 5 and 6.

The pieces 5 and 6 comprise at the base of the core, respectively 53, 63 of each, a groove respectively 54, 64 extending over their entire length. These grooves are located at the end of the core and above the shortest wing respectively 52, 62, such that they are opposite one another and constitute a type of slide capable of holding a piece approximately rectangular in cross-section, forming a lid for closing of the light box formed by the parallel faces 55 and 65 of the pieces 5 and 6. This lid 7 is installed in the housing constituted by the grooves 54, 64. This lid is made of a translucent and diffusing material so as to fulfill the function of a film generating a certain diffusion of light beams passing through it. According to the invention it could advantageously be made from a roughened transparent material such as roughened Plexiglas.

Since the light-emitting diodes 4 are aligned and all fixed in the same way their axes are substantially parallel and constitute a plane $p_1$. This plane is a plane of symmetry for the light box and it shares the conduit constituted by the faces 55 and 65 respectively of the pieces 5 and 6, in its middle, as well as the translucent lid 7. The grooves 54, 64 and the pieces 5 and 6 all have their sides calculated so that the lid 7 is in a plane perpendicular to plane $P_1$ formed by the axes of the light-emitting diodes.

A piece constituting a reflector 8 is fixed onto the core 63 of the piece 6. This piece 8 is substantially the same length as the pieces 5 and 6; it is rectilinear and its cross-section comprises an outer face of general convex form and an inner face 81 of general concave form. According to a preferred mode of the invention, the inner face 81 opposite the fixing side has the form of a straight parabolic cylinder.

This means that all the straight sections of its inner face are parabolas.

Because the surface 81 is a straight parabolic cylinder the axes of each parabolic section constitute an axial plane $P_2$ and the piece 8 is fixed on the piece 6 so that this plane $P_2$ is perpendicular to the plane $P_1$ and so that the surface 81 is opposite the row of light-emitting diodes 4 and of the diffuser 7, as is illustrated in FIG. 3. The lower surface 81 of the reflector 8 is polished or coated by a deposit allowing it to have the reflecting properties of a mirror. The reflector 8 is fixed on the core of the piece 6 by bolting, as is illustrated in FIG. 3, so as to facilitate regulating and alignment. This fixing is located to the side of the face opposite the face 81 in the form of a straight parabolic cylinder, so as to allow the passage of light beams from the other side. Naturally, other modes of fixing giving the same results can also be imagined.

The light-emitting diodes 4 are arranged side by side according to a pitch which depends on their size and on their power, in such a way that the volumes of revolution of their radiation resect widely and this resection is easy to determine since the distribution of the radiation about the axis of each diode has the allure of a Gauss curve. The light flux is oriented according to the direction of the plane $P_1$ by the reflections on the reflecting faces 55 and 65 of the pieces 5 and 6, nevertheless the resulting light flux presents intensity undulations with local maxima located in the axis of each diode. These undulations are widely attenuated after passage of the light beams through the film 7. The optimal distance between the diodes and the diffusing film to make this attenuation is a function of the implantation pitch of the diodes and the wings 52, 54 respectively 62, 64 of the pieces 5, respectively 6 are dimensioned to bring this about. The characteristics and the thickness of the film 7 are defined also for this same lens. A linear source of diffuse light is made thus at the outlet of the film 7.

It is known furthermore that the light beams coming from a localized source reflect onto a parabolic mirror in that they all take the same direction, which is that of the axis of the parabola, when the source is placed in the focal spot of said parabola. The reflector 8 whereof the inner surface 81 is a straight parabolic cylinder is therefore installed such that the focal spot is located substantially in the center of the outlet face of the light beams of the film 7. In practical terms the surface 81, which is a straight parabolic cylinder, is calculated and arranged so that the axis of the focal spots of the parabolas is substantially located at the intersection of the planes $P_1$ and $P_2$. Therefore, all the beams passing through the film 7 will be reoriented in a direction parallel to the plane $p_2$ forming a lighting spot beam whereof the beams will be in general parallel to one another and whereof the thickness depends on the characteristics of the surface 81. This thickness will be determined as a function of the distance from the striplight R at which the strip S to be illuminated is situated. The result is thus a lighting zone substantially in the desired form and illustrated in FIG. 2. The characteristics of this lighting zone do not need precise regulating of the distance between the striplight and the strip, nor focusing of the light beam since this is a barely divergent spot beam.

According to the distance between the striplight R and the strip S and the zone to be illuminated light-emitting diodes of different power could be selected, and diodes of unit power of 1, 3 or 5 watts could be installed. It is also possible to select the color of the diodes to resolve problems of parasite light of ambient lighting of the workshop in which the fault detection device must be installed. Diodes of red, green or white color can thus be used, as is current practice. A filter of the same color is then installed in the linear camera C.

Advantageously, the outer wing 61 of the piece 6 has been designed greater in height than the outer wing 51 of the piece 5 to be able to fix the supply modules of the diodes in the immediate vicinity of said diodes.

In fact, and according to a preferred embodiment of the invention, the diodes are connected in series to form chains, which are each fed by an adjustable current feed. The light flux emitted by a light-emitting diode depends on the temperature of the junction and, to maintain good luminous yield, this junction temperature will be maintained by regulating the current, at a value less than 80° C.

Fixed to the two ends of the support chassis 1 are circular terminals 12 which close the striplight assembly in a tube 13 fixed on the terminals 12. The tube 13 is fitted with an opening 9 arranged over its entire length serving as window for passage of light beams. This window is closed by a transparent 10. The assembly is made tight by conventional jointing processes and ventilation and cooling or acclimatization devices are provided for keeping the temperature substantially constant inside the striplight R and avoiding overheating of the light-emitting diodes and the various components. These ventilation and cooling devices, not illustrated in the figures, are well known and produced conventionally, and do not need to be described in further detail. Temperature sensors are also installed in the striplight R at critical sites for measuring the average internal temperature and ensuring thermal security of the components.

Finally, mechanical fixing means, not illustrated, enable installing the striplight in the region of the equipment on which it must function. These fixing means allow orientation and adjusting of the lighting zone on the portion of the scrolling product to be observed.

It is understood that the invention is not limited to the embodiment, which has just been described by way of example and can apply to the detection of faults of products made of steel or constituted by another metal and in different forms, without departing from the scope of the invention.

The invention can also be applied to any product of another material or made by a process other than laminating, such as for example extrusion of plastic materials, requiring the use of auxiliary lighting.

It is also possible to use other configurations of the components inside the striplight or other forms of diffuser and reflector, as well as other solutions for assembling and mechanically fixing these components, without departing from the scope of the invention.

The sole purpose of the reference signs inserted after the technical characteristics mentioned in the claims is to facilitate comprehension of the latter, and they do not at all limit their scope.

The invention claimed is:

1. A lighting device of a scrolling product for the detection of surface faults constituted by a closed mechanical support assembly forming an elongated box constituting a striplight and comprising:
    a plurality of high-power light-emitting diodes aligned in at least one row and arranged side by side according to a regular pitch;
    a light guide with flat and reflecting walls, parallel to one another and located in planes substantially parallel to a plane formed by axes of the light-emitting diodes;
    a film made of translucent and diffusing material arranged on a trajectory of light beams emitted by the light-emitting diodes;
    a reflector for concentrating and sending back the light beams to an exterior of a closed support through a window forming an elongated opening arranged substantially over a length of the striplight; and
    a transparent lid for closing the opening arranged in the striplight while letting the light beams emanating from the light-emitting diodes pass to the exterior.

2. The lighting device of a scrolling product as claimed in claim 1, wherein the walls of the light guide are made of polished metal.

3. The lighting device of a scrolling product as claimed in claim 1, wherein the film diffusing material is made of roughened transparent material formed from a thermoplastic polymer of methyl methacrylate.

4. The lighting device of a scrolling product as claimed in claim 1, wherein a surface of the reflector has the form of a straight parabolic cylinder.

5. The lighting device of a scrolling product as claimed in claim 4, wherein an axial plane of the parabolic reflector is substantially perpendicular to the plane defined by the axes of the light-emitting diodes.

6. The lighting device of a scrolling product as claimed in claim 5, wherein an intersection of the plane defined by the axes of the diodes with the axial plane of the reflector is located substantially on an axis joining focal spots of the parabolic sections of the reflector.

7. The lighting device of a scrolling product as claimed in claim 1, wherein the mechanical support assembly is closed by an envelope constituted by an airtight tube blocked at two ends of said tube and provided with a window fitted with a transparent pane arranged substantially over an entire length of said envelope for letting through illuminating light.

8. The lighting device of a scrolling product as claimed in claim 7, wherein the air-tight tube is ventilated and cooled.

9. The lighting device of a scrolling product as claimed in claim 1, wherein the light-emitting diodes are connected electrically in series in groups and form a chain.

10. The lighting device of a scrolling product as claimed in claim 9, wherein each chain is fed by an adjustable current controller.

11. The lighting device of a scrolling product as claimed in claim 7, wherein temperature sensors are installed in the air-tight tube to measure average internal temperature.

12. The lighting device of a scrolling product as claimed in claim 1, wherein the assembly of the striplight comprises adjustable fixing means for orienting and adjusting the lighting of a zone to be observed.

13. A process for lighting in cold light of a scrolling product for the acquisition of images of the surface of said product by linear digital cameras for a fault detection system, said process comprising the steps of:
    providing a lighting device of a scrolling product for the detection of surface faults constituted by a closed mechanical support assembly forming an elongated box constituting a striplight and comprising a plurality of high-power light-emitting diodes aligned in at least one row and arranged side by side according to a regular pitch, a light guide with flat and reflecting walls, parallel to one another and located in planes substantially parallel to a plane formed by axes of the light-emitting diodes, a film made of translucent and diffusing material arranged on a trajectory of light beams emitted by the light-emitting diodes, a reflector for concentrating and sending back the light beams to an exterior of a closed support through a window forming an elongated opening arranged substantially over a length of the striplight, and a transparent lid for closing the opening arranged in the striplight while letting the light beams emanating from the light-emitting diodes pass to the exterior;

arranging the light-emitting diodes in said at least one row to be aligned according to equal intervals in a housing constituting a light box with said reflecting walls;

producing a slight diffusion of light coming from the light-emitting diodes by said film closing the light box; and concentrating the light beams emanating from the light box using said reflector into a flat and narrow lighting spot beam having a width substantially equal to the length occupied by the alignment of the diodes.

14. The process for lighting a scrolling product as claimed in claim 13, further comprising determining a distance from the film closing the light box with light-emitting diodes as a function of an implantation pitch of said light-emitting diodes.

15. The process for lighting a scrolling product as claimed in claim 13, arranging the light beams constituting a lighting spot beam to be substantially parallel to one another.

16. The process for lighting a scrolling product as claimed in claim 13, wherein the light-emitting diodes arranging step comprising making all of said diodes the same color.

17. The process for lighting a scrolling product as claimed in claim 16, wherein said making step comprises making the light-emitting diodes from a color selected from the group consisting of white, red and green.

18. The process for lighting a scrolling product as claimed in claim 13, further comprising electrically connecting the light-emitting diodes in series in groups constituting a chain.

19. The process for lighting a scrolling product as claimed in claim 18, further comprising providing the light-emitting diodes with an equal unit power and of a value of 1, 3 or 5 Watts.

* * * * *